(12) United States Patent
Claus et al.

(10) Patent No.: US 8,430,841 B2
(45) Date of Patent: Apr. 30, 2013

(54) APPLICATION OF VACUUM AS A METHOD AND MECHANISM FOR CONTROLLING EYE CHAMBER STABILITY

(75) Inventors: Michael J Claus, Newport Coast, CA (US); Wayne S Wong, Irvine, CA (US); Carina R Reisin, Tustin, CA (US); Stephen H Jang, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 187 days.

(21) Appl. No.: 12/695,812

(22) Filed: Jan. 28, 2010

(65) Prior Publication Data

US 2010/0130915 A1 May 27, 2010

Related U.S. Application Data

(62) Division of application No. 11/086,508, filed on Mar. 21, 2005, now Pat. No. 7,670,330.

(51) Int. Cl.
*A61M 1/00* (2006.01)

(52) U.S. Cl.
USPC .............................. 604/35; 604/27; 604/118

(58) Field of Classification Search ............ 604/27, 604/28, 30, 31, 35, 521, 65, 66, 67, 118, 604/119, 120; 606/107
See application file for complete search history.

(56) References Cited

U.S. PATENT DOCUMENTS

| | | | |
|---|---|---|---|
| 4,832,685 A | 5/1989 | Haines |
| 4,935,005 A | 6/1990 | Haines |
| 5,032,111 A | 7/1991 | Morris et al. |
| 5,047,009 A | 9/1991 | Morris et al. |
| 5,569,188 A | 10/1996 | Mackool |
| 5,700,240 A | 12/1997 | Barwick, Jr. et al. |
| 5,733,256 A | 3/1998 | Costin |
| 5,865,764 A | 2/1999 | Moorhead |
| 6,179,808 B1 | 1/2001 | Boukhny et al. |
| 6,491,661 B1 | 12/2002 | Boukhny et al. |
| 6,579,255 B2 | 6/2003 | Kadziauskas et al. |
| 6,648,223 B2 | 11/2003 | Boukhny et al. |

(Continued)

FOREIGN PATENT DOCUMENTS

| | | |
|---|---|---|
| JP | 62500640 T | 3/1987 |
| JP | 2001161740 A2 | 6/2001 |

(Continued)

OTHER PUBLICATIONS

PCT International Search Report for application No. PCT/US07/66248, Mailed on Aug. 30, 2007, 4 pages.

(Continued)

*Primary Examiner* — Bhisma Mehta
(74) *Attorney, Agent, or Firm* — Abbott Medical Optics Inc.

(57) ABSTRACT

A phacoemulsification system for operating a surgical handpiece having a handpiece; an irrigation fluid source for supplying irrigation fluid to the eye; an aspiration source coupled to the handpiece in order to aspirate the irrigation fluid from the eye through the handpiece; and a controller for controlling a vacuum in the handpiece, the controller comprising: a sensor for sensing the vacuum in the handpiece; an occlusion parameter, the occlusion parameter being a vacuum level corresponding to an occlusion of the handpiece or a flow rate corresponding to an occlusion of the handpiece; a maximum allowable vacuum level in the handpiece, the maximum allowable vacuum level having at least a first predetermined level; and a trigger value that is set based in part on the occlusion parameter.

8 Claims, 4 Drawing Sheets

U.S. PATENT DOCUMENTS

| | | |
|---|---|---|
| 6,780,166 B2 | 8/2004 | Kanda et al. |
| 7,297,137 B2 | 11/2007 | Gordon et al. |
| 2002/0193817 A1 | 12/2002 | Lal et al. |
| 2003/0050619 A1 | 3/2003 | Mooijman et al. |
| 2003/0105437 A1 | 6/2003 | Neubert |
| 2004/0092921 A1 | 5/2004 | Kadziauskas et al. |
| 2005/0080375 A1 | 4/2005 | Kadziauskas et al. |
| 2005/0118048 A1 | 6/2005 | Traxinger |
| 2005/0209621 A1 | 9/2005 | Gordon et al. |
| 2005/0261715 A1 | 11/2005 | Boukhny et al. |
| 2005/0267504 A1 | 12/2005 | Boukhny et al. |
| 2006/0224107 A1 | 10/2006 | Claus et al. |
| 2006/0224143 A1 | 10/2006 | Claus et al. |

FOREIGN PATENT DOCUMENTS

| | | |
|---|---|---|
| JP | 2001212169 | 8/2001 |
| JP | 2003225256 A2 | 8/2003 |
| WO | WO9945868 A1 | 9/1999 |
| WO | WO-2004108189 A2 | 12/2004 |
| WO | WO-2004110524 A2 | 12/2004 |
| WO | WO-2005037156 A1 | 4/2005 |

OTHER PUBLICATIONS

Office Action mailed Mar. 15, 2011 for Japanese Application No. 2008503035 filed Mar. 14, 2006.

APPLICATION OF VACUUM AS A METHOD AND MECHANISM FOR CONTROLLING EYE CHAMBER STABILITY

This application claims priority to and is a divisional application of U.S. application Ser. No. 11/086,508, filed on Mar. 21, 2005, now U.S. Pat. No. 7,670,330, issued Mar. 2, 2010, the entirety of which is hereby incorporated by reference.

BACKGROUND

Embodiments of the present invention are generally directed to surgical methods and are more particularly directed to controlling the flow of fluid to and from a patient through a fluid infusion and extraction system such as, for example, in ophthalmic surgery wherein surgical instruments such as electromechanical or pneumatically driven cutters as well as phacoemulsification instruments are commonly employed. These instruments require a source of fluid to infuse a surgical site and a source of negative pressure to evacuate the infused liquid and debris from the site. A pump is usually employed to generate negative pressure. Typical pumps are either flow pumps, such as, for example, peristaltic or scroll pumps, or vacuum pumps, such as, for example Venturi pumps, diaphragm pumps or rotary vane pumps.

A number of medically recognized techniques are utilized for cataractic lens removal based on, for example, phacoemulsification, mechanical cutting or destruction, laser treatments, water jet treatments, and so on.

The phacoemulsification method includes making a corneal incision and the insertion of a phacoemulsification handpiece which includes a needle that is ultrasonically driven in order to emulsify, or liquefy, the lens. Concomitantly, fluid is irrigated into the eye and the irrigation fluid and liquefied lens material are aspirated from the eye. Other medical techniques for removing cataractous lenses also typically include irrigating the eye and aspirating lens parts and other liquids. Additionally, some procedures may include irrigating the eye and aspirating the irrigating fluid without concomitant destruction, alteration or removal of the lens.

As is well known, for these various techniques it is necessary to maintain a stable volume of liquid in the anterior chamber of the eye and this is accomplished by irrigating fluid into the eye at the same rate as aspirating fluid and lens material. For example, see U.S. Pat. No. 5,700,240 which is incorporated herewith, in toto, by this specific reference thereto. FIG. 4 is similar to FIG. 1 of U.S. Pat. No. 5,700,240 and illustrates phacoemulsification system 60 including a control unit 62, indicated by the dashed lines in FIG. 4 which includes a variable speed peristaltic pump 64, which provides a vacuum source, a source of pulsed ultrasonic power 66, and a microprocessor computer 68 that provides control outputs to pump speed controller 70 and ultrasonic power level controller 72. A vacuum sensor 74 provides an input to computer 68 representing the vacuum level on the output side of peristaltic pump 64. Suitable venting is provided by vent 76. Also shown is eye 86, handpiece 80, irrigation fluid source 82, aspiration lines 88 and 90, irrigation line 84, ultrasonic power line 78, and output line 92.

During this procedure, it is possible for the aspirating phacoemulsification handpiece to become occluded. This occlusion is caused by particles blocking a lumen or tube in the aspirating handpiece. This blockage can result in increased vacuum (i.e. increasingly negative pressure) in the aspiration line and the longer the occlusion is in place the greater the vacuum. Once the occlusion is cleared, a resulting rush of fluid from the anterior chamber into the aspiration line can outpace the flow of new fluid into the eye from the irrigation source.

The resulting imbalance of incoming and outgoing fluid can create a phenomenon known as post-occlusion surge or fluidic surge, in which the structure of the anterior chamber moves rapidly as fluid is replaced. Such post-occlusion surge may lead to eye trauma. Current precautions against post-occlusion surge cause cataract surgery to be lengthier and more difficult for an attending surgeon.

Alternate surgical procedures, when an occlusion occurs, typically include a reduction of aspiration rate to a level less than the irrigation rate before continuing the procedure. This can be accomplished by changing the aspiration rate setting on the system. This, in turn, allows the pump to run slower and the fluid volume in the anterior chamber to normalize. Other alternate surgical systems may employ a restriction in the aspiration circuit to restrict surge flow when an occlusion clears from the aspiration tube.

Alternative techniques heretofore utilized include a reduction of vacuum on the occlusion by adjusting system settings. This technique often requires an assistant to perform the actual modification of settings.

Still another technique for vacuum control can be accomplished by reducing pressure on a control footpedal or releasing a footpedal altogether. This technique, however, requires a surgeon to discontinue applying ultrasonic power temporarily until the occlusion is either cleared or has been released from the aspirating phacoemulsification handpiece.

A disadvantage in releasing the footpedal is the fact that cataract lens material in the aspirating phacoemulsification handpiece may flow back into the eye chamber.

In addition, the combination of the hereinabove recited techniques may be employed as well. However, once an occlusion occurs, the surgeon must identify the cause and then take corrective action. However, the length of time before the occlusion clears varies. In the time it takes for a surgeon to identify the cause and request corrective action, the occlusion can build sufficient vacuum and then clear, thus resulting in post occlusion surge.

As a result, surgeons tend to operate their phacoemulsification systems at lower vacuum levels than otherwise preferable in order to avoid this problem. The present invention overcomes the disadvantages of operating surgical handpieces, as hereinabove identified.

SUMMARY OF THE INVENTION

A method in accordance with the present invention is directed to operating one or more surgical handpieces including at least 1) an aspiration source, 2) a source of irrigating fluid, and 3) a control unit having a vacuum sensor and/or a flow rate sensor. The aspiration source is typically a flow pump or a vacuum pump, such as, for example, a peristaltic pump or a Venturi pump, respectively, or a combination of the two. One or more of the surgical handpieces may further include a surgical device for cutting, moving, ablating, altering, measuring or treating tissue, and often such surgical devices will require a power source.

Embodiments of the method for application to opthalmology generally include placing a surgical handpiece in an operative relationship with an eye for a selected surgical procedure. The handpiece may include a phacoemulsification device or an electromechanical, laser, water jet or pneumatically driven cutter suitable for the selected ophthalmic procedures.

A method in accordance with the present invention further includes supplying irrigation fluid from the irrigation fluid source to the eye and providing power from the power source to the handpiece for performing the surgical procedure. In some embodiments, irrigation and aspiration take place without other surgical procedures being applied. Further, some treatments may involve bi-manual processes in which the surgeon uses devices in both hands, such that one device may include, for example, a phacoemulsification mechanism and aspiration source and the other device in the other hand includes an irrigation source, or other combinations thereof.

An aspirating force is applied by the aspirating source through the handpiece in order to aspirate the irrigation fluid from the eye, and during fluid aspiration a vacuum pressure level and/or a flow rate is sensed. Such vacuum pressure and/or flow rate are used in part to detect an occlusion of the handpiece.

More specifically, in accordance with the present invention, a duration of an occlusion is determined from the sensed vacuum level (typically a rise in vacuum pressure, (i.e. an increasingly negative pressure)) and/or a sensed flow rate (i.e. a drop in flow rate for a constant vacuum pressure), and in response thereto, at least one of the 1) supply of irrigation fluid, 2) vacuum level, 3) aspiration rate, and 4) power applied to the handpiece is/are controlled.

More particularly, the vacuum may be controlled by lowering a maximum level of vacuum allowed during an occluded state of a surgical procedure. In addition, a method in accordance with the present invention may include further determining a vacuum drop from the sensed vacuum level and/or a flow rate rise from the sensed flow rate, either or both of which typically indicate a clearance of the occlusion, and in response to the vacuum dropping below and/or flow rate rising above a threshold, increasing the level of aspirating force (i.e. increasing vacuum pressure).

Further, a method in accordance with the present invention may include manipulating an occluding particle with another separate instrument in order to clear the occlusion during the lowered maximum level of vacuum.

Alternatively, in accordance with the present invention during the lowered maximum level of vacuum a supply of irrigation fluid may be varied as well as in combination or separately varying the aspiration rate and in combination or separately varying the power applied to the handpiece.

BRIEF DESCRIPTION OF THE DRAWINGS

The advantages and features of the present invention will be better understood with the following detailed description when considered in conjunction with the accompanying drawings of which.

DETAILED DESCRIPTION

Figure 1:
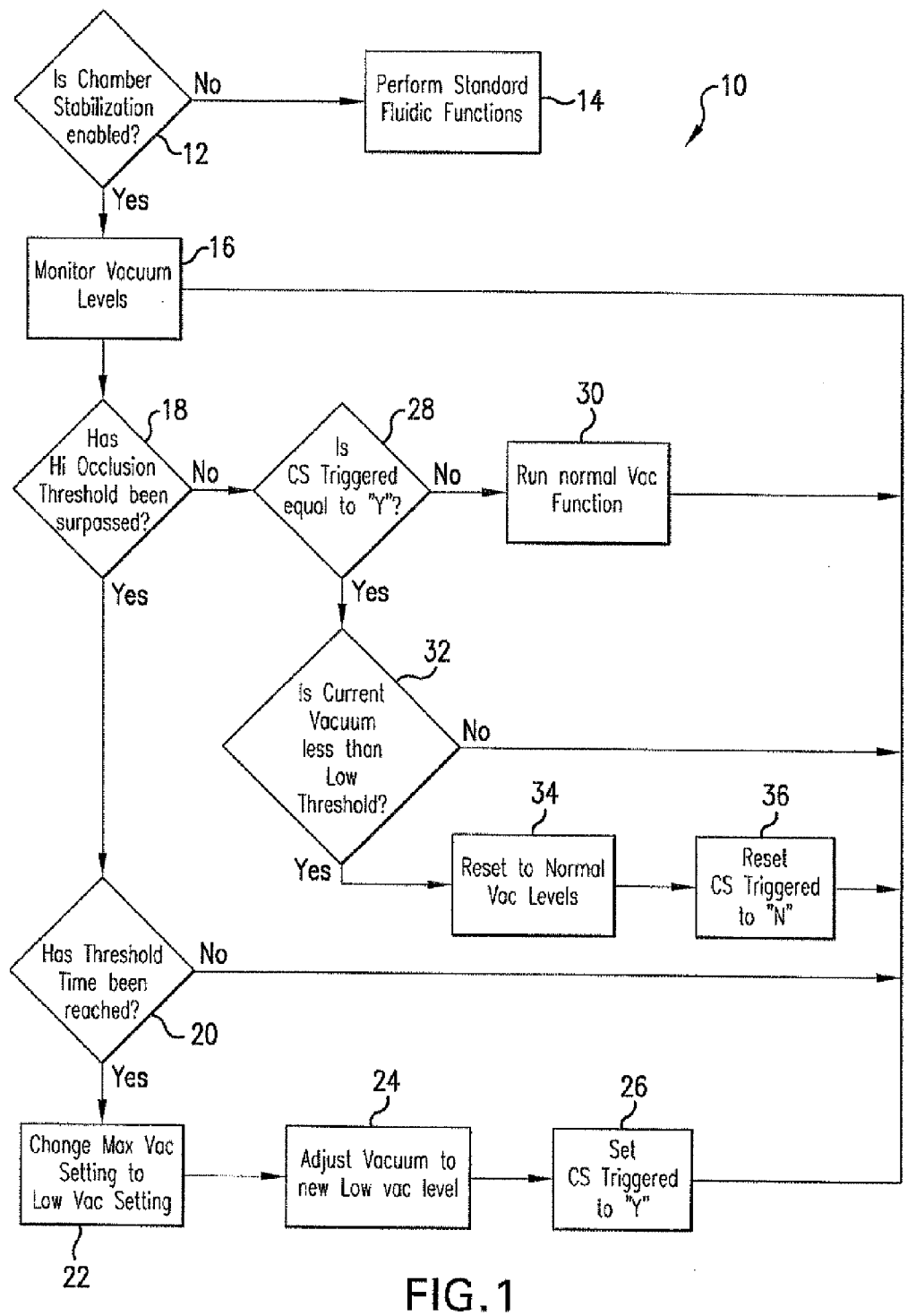
FIG. 1 is a block diagram of one embodiment of the present invention.

As illustrated in FIG. 1, a block diagram 10 sets forth a method in accordance with the present invention. It should be appreciated that the present method applies to controlling at least one of: 1) the supplied irrigation fluid, 2) vacuum, 3) aspiration rate, and 4) the power applied to a handpiece in an ophthalmic surgery procedure. Only one of the control features being set forth for the sake of brevity. The aspiration force may be provided by any type of fluid pump, including flow pumps and vacuum pumps.

As shown in FIG. 1, a system or method may include a pre-determined or user-chosen setting (for example, a setting labeled here as "Chamber Stabilization" or "CS") to turn on or off the various embodiments of the present invention. If a user turns off this CS setting (i.e. CS is not enabled (12)), then standard fluidic functions (14) are performed without the benefit of the embodiments described herein.

In accordance with a method of the present invention during surgery employing a flow pump (e.g., peristaltic pump), and if the user sets the system to employ said methods (i.e. CS enabled (12)), vacuum is monitored (16) and as particles are aspirated, vacuum levels in the aspiration handpiece will fluctuate. When the aspirating handpiece becomes occluded, i.e. partially or fully blocked, vacuum will rise. An occlusion threshold value may be pre-set in the system or entered into the system. The occlusion threshold value is the value at which the vacuum level is recognized by the system and/or user as indicating that an occlusion has occurred. In other words, as the monitored vacuum increases, the occlusion threshold value is the value of the monitored vacuum at which the aspiration tube has been completely or substantially (e.g., greater than 50%, and preferably greater than 80%) occluded. If vacuum continues to rise until it reaches a maximum allowable vacuum (Max Vac), then the pump is typically stopped. A Max Vac setting may be pre-determined or programmed in the system by a user before or during a surgical procedure. The occlusion threshold may be set at or below the same level as the Max Vac setting. In some embodiments the Max Vac level and occlusion threshold value are set to the same level. Alternately, the occlusion threshold value is set at a percentage (i.e. ≦100%) of the Max Vac level, such as, for example, in a range between about 20% to about 95%. Alternately, the occlusion threshold may be pre-determined at or programmed to a set vacuum level.

Alternate embodiments for systems using vacuum pumps (e.g., Venturi pumps), flow rate is monitored (not shown in FIG. 1) instead of vacuum level. When the aspirating handpiece becomes occluded, i.e. partially or fully blocked, flow rate will decrease. An occlusion flow rate threshold value may be pre-set in the system or entered into the system. The occlusion flow rate threshold value is the value at which the flow rate is recognized by the system and/or user as indicating that an occlusion has occurred. In other words, as the monitored flow rate decreases, the occlusion flow rate threshold value is the value of the monitored flow rate at which the aspiration tube has been completely or substantially occluded.

In embodiments for combination systems using vacuum pumps and flow pumps, a control unit may control operation by monitoring an occlusion parameter such as one or both of the vacuum level and flow rate and may employ the above-described methods of determining occlusion.

In any case, when an occlusion occurs (18), the duration of the occlusion is determined (20) in flow pump systems by measuring the amount of time starting from the time when the monitored vacuum rises above the occlusion threshold value and in vacuum pump systems when the monitored flow rate falls below the occlusion flow rate threshold value. After the passing of a programmed or predetermined period of time, (herein referenced as a threshold time ($t_T$)) has elapsed, the maximum allowable vacuum level is automatically reduced

(22) to a user programmable new maximum vacuum (Low Vac) level (24). This causes less vacuum around the particle occluding the aspiration handpiece. Reducing vacuum may occur through various known actions, such as, for example: by venting the vacuum; by allowing air or fluid into the vacuum area (e.g., between the occlusion and the pump); by reversing pump flow; and/or by lowering the vacuum setting in the case of vacuum pumps, such as a Venturi pump. The threshold time ($t_T$) is typically in a range between tens of milliseconds and hundreds of milliseconds, and preferably in a range between about 50 milliseconds and about 300 milliseconds. A trigger value (26) may be set to indicate that the maximum allowable vacuum level has been reduced to a lower level (i.e. Low Vac). The system then returns to monitoring vacuum (16) as treatment continues.

During this period of time, there has been no change in the surgeon's foot pedal (not shown) position nor has an assistant been required to modify any setting on the system. Accordingly, the method in accordance with the present invention provides the advantage of reducing manual input and accordingly enables the physician to concentrate on the procedure.

The Low Vac level should be set to a level with sufficient vacuum to hold the particle and allow the surgeon to separately or in combination: 1) vary phaco power (or more generally the power to the handpiece surgical mechanism (i.e. laser, cutters, etc.), 2) vary the aspiration rate, and/or 3) vary the irrigation rate as required to clear the occlusion. The method will typically not allow the vacuum level to rise above the low vac level until the occlusion has cleared.

When the occlusion is cleared, the system is operating at the Low Vac level where the potential for post occlusion surge is minimized. In addition, in flow pumps (e.g., peristaltic pumps) after the occlusion is cleared, the actual vacuum level in the aspiration line will drop. In vacuum pumps (e.g., Venturi pumps), the flow rate will rise after the occlusion has cleared. In combination systems using both types of pumps, either or both a vacuum drop or a flow rate increase may be measured after the occlusion is cleared.

In one embodiment in accordance with the present invention, the vacuum drop in a flow-type pump system is identified by determining when it falls below a user programmable or pre-set minimum vacuum threshold (Low Threshold) (32), at which point an original user-programmed maximum allowable vacuum aspiration level (Max Vac) is typically reinstated. In an alternate embodiment employing a vacuum pump, the flow rate increase is identified by determining when the flow rate rises above a user programmable or pre-set minimum flow rate threshold (Low Flow Rate Threshold), at which point an original user-programmed maximum allowable vacuum aspiration level (Max Vac) is typically reinstated. As shown in FIG. 1 for a flow pump system, when the monitored vacuum is below the occlusion threshold value (18), the system checks to determine if Low Vac is set (28), i.e. has the CS trigger been set to "on" or "yes". If not, then normal vacuum and fluid functions are continued (30). If Low Vac is the current setting and the monitored vacuum level is below a Low Threshold (32), Max Vac is re-set (34) and the CS trigger is re-set to "no" or "off" (36). If monitored vacuum is not below Low Threshold, then vacuum monitoring continues. In vacuum pump embodiments, when monitored flow rate is above the occlusion flow rate threshold, the system checks to determine if Low Vac is set, and if not, then normal vacuum and fluid functions are continued. If Low Vac is the current setting, then Max Vac is re-set. Note that while FIG. 1 primarily depicts embodiments for flow pump systems, it also works for vacuum pump systems if block 16 is changed to include monitoring flow rate, block 18 is changed to include occlusion flow rate threshold, and block 32 is changed to include current flow rate greater than Low Flow.

Figure 2:
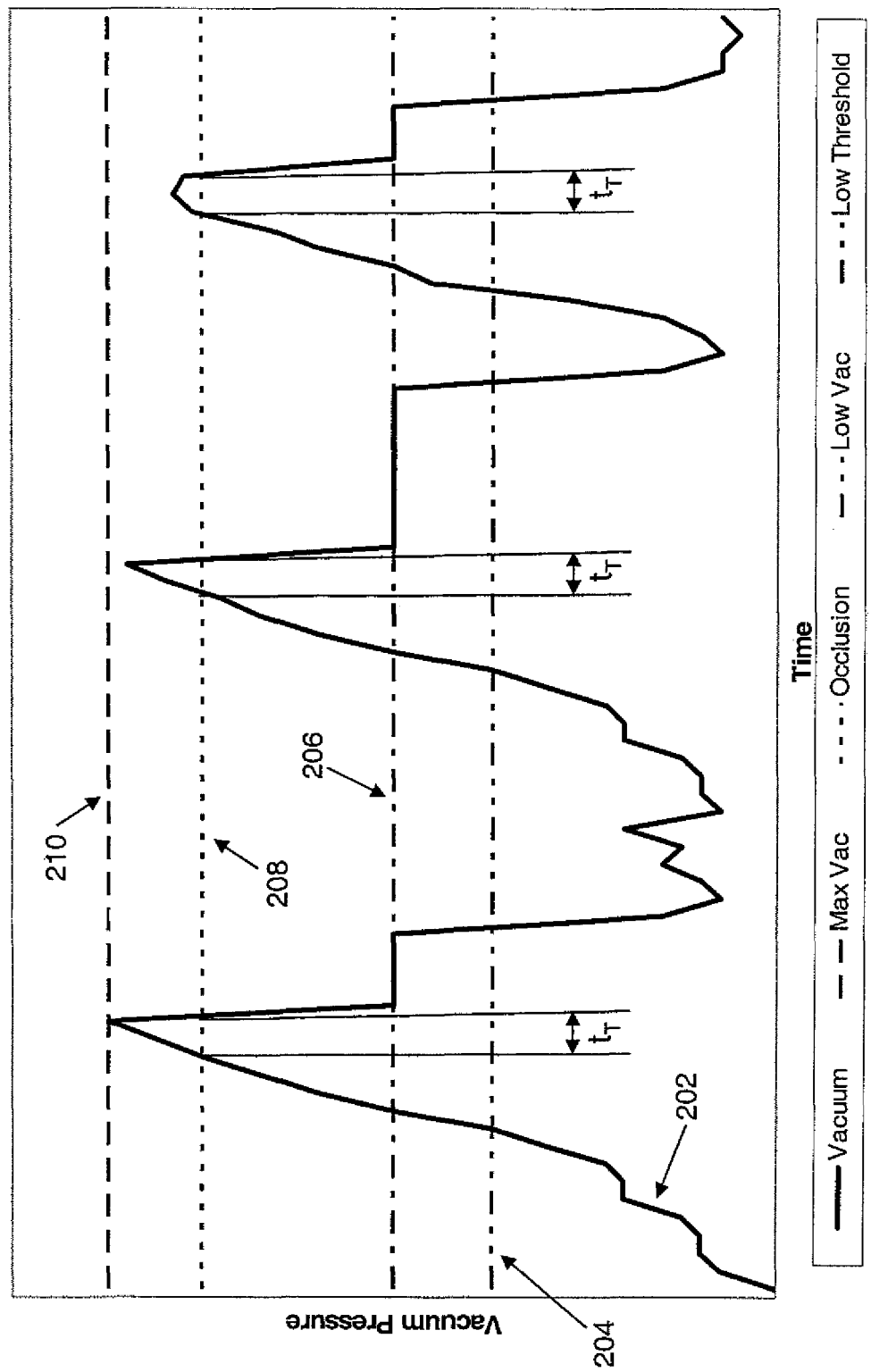
FIG. 2 is a graph showing the vacuum pressure relative to various system settings in an embodiment of the present invention.
Figure 3:
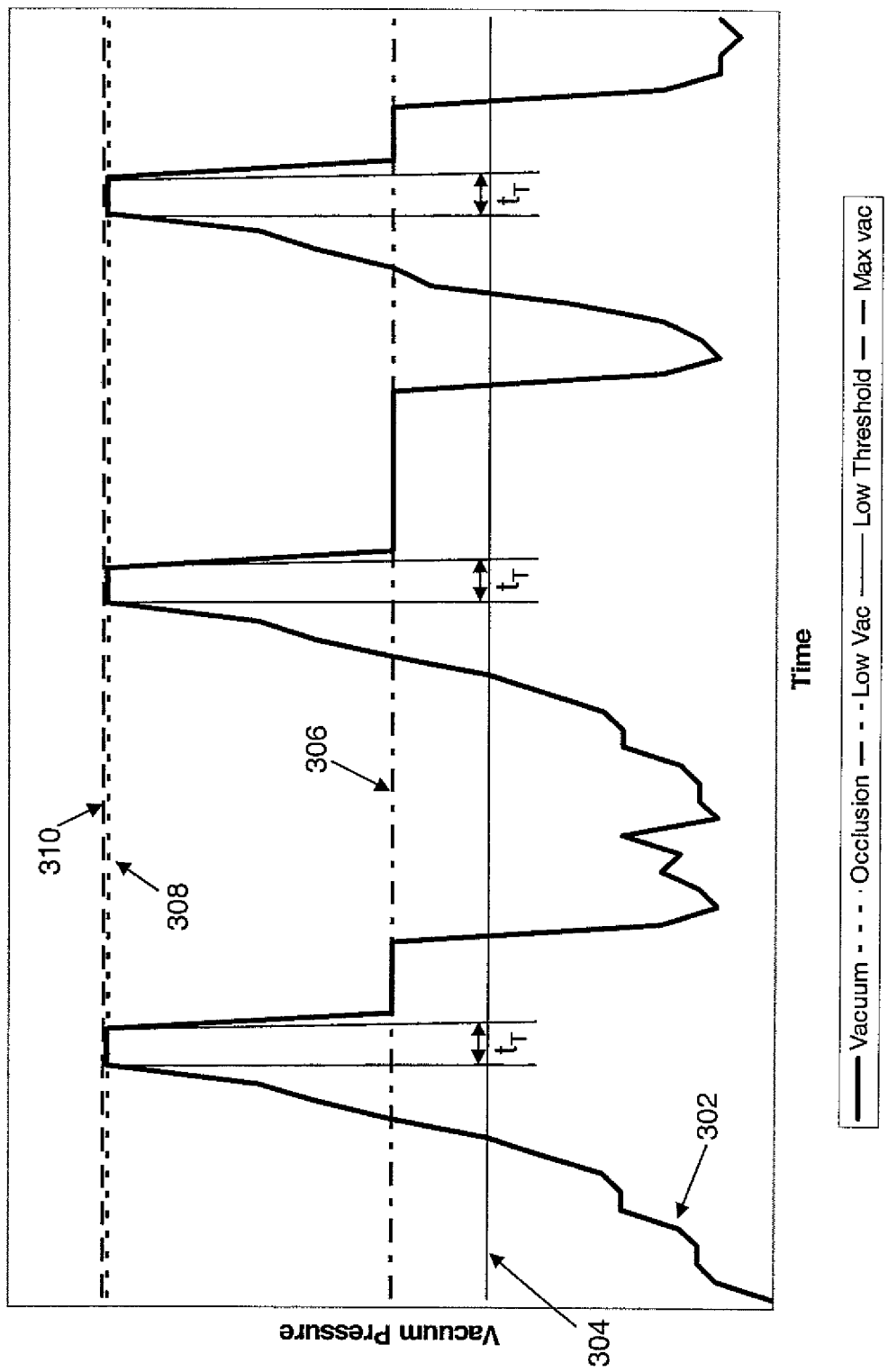
FIG. 3 is a graph showing the vacuum pressure relative to various system settings in an embodiment of the present invention.
Figure 4:
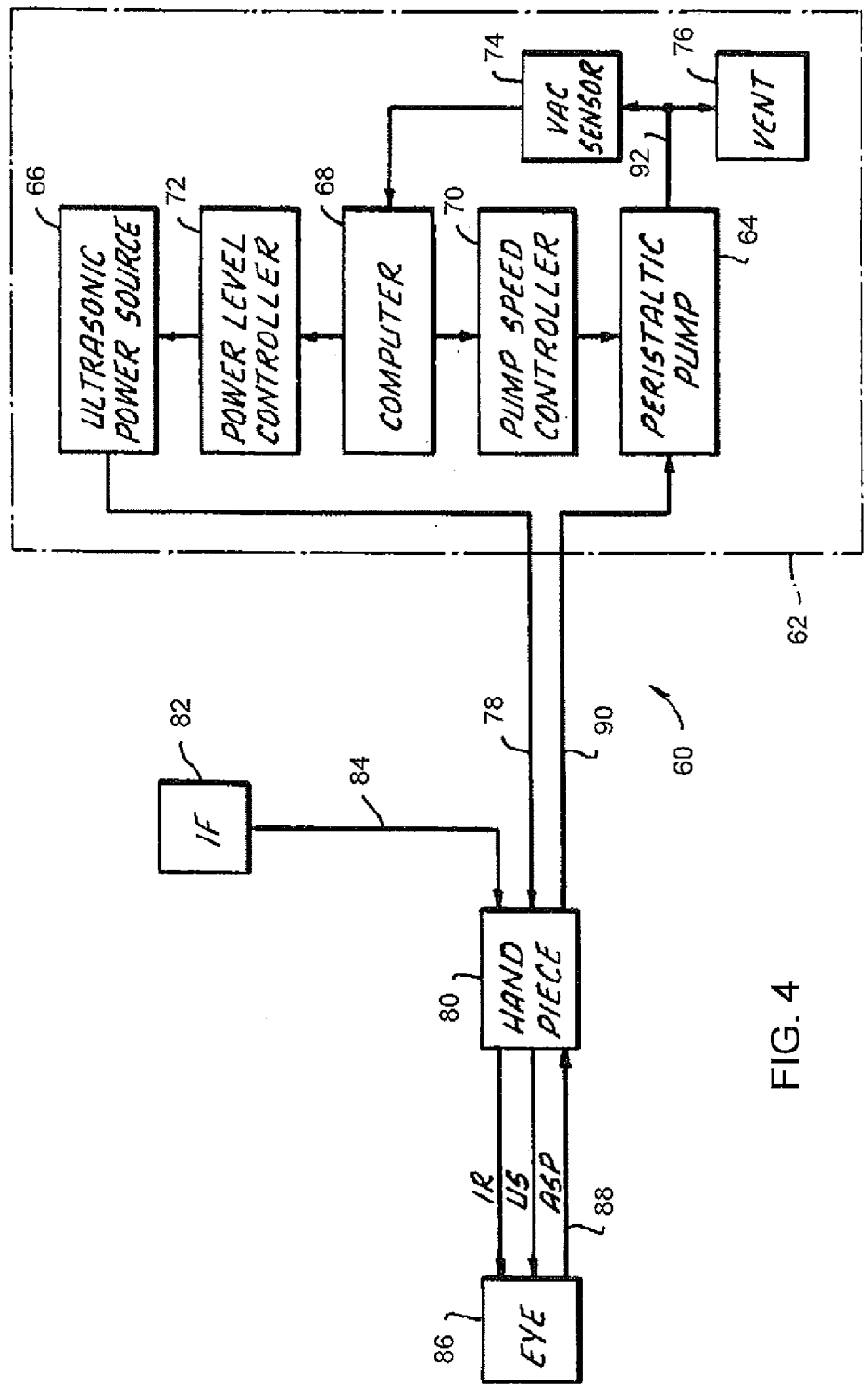
FIG. 4 is a functional block diagram of a phacoemulsification system for operating a surgical handpiece.

FIGS. 2 and 3 depict graphical examples of monitored vacuum levels in accordance with the various embodiments of the present invention. FIG. 2 shows an example in which Max Vac (210) is set at a level above occlusion threshold (208). Low Vac (206) and Low Threshold (204) are also pre-determined or programmed. The monitored vacuum is line 202. Starting at the left side of FIG. 2 and following monitored vacuum 202 to the right, as vacuum 202 rises during a procedure and crosses occlusion threshold 208, the system recognizes that an occlusion has begun and a timer begins measuring the time. If vacuum 202 reaches the Max Vac level (not shown), then the pump may be turned off and the maximum allowable vacuum level may be re-set to Low Vac. If Max Vac is not exceeded and once the measured time has passed the threshold time ($t_T$), then the maximum allowable vacuum level is dropped to the Low Vac level, thereby reducing the monitored vacuum 202. Alternately, the Low Vac may be set without waiting for a threshold time to pass, in which case a timer would not be needed. As the occlusion is cleared by whatever means, vacuum 202 begins to drop again until it falls below Low Threshold (204). At that point, the system recognizes that the occlusion has been cleared, and Max Vac is re-set as the maximum allowable vacuum level. The monitored vacuum level 202 typically stays at the lower level in flow pump systems until another occlusion is encountered. When another occlusion is encountered, the vacuum 202 begins to rise again and the process stated above begins anew.

FIG. 3 shows a similar example to that of FIG. 2, with the difference that the Max Vac value (310) and the occlusion threshold value (308) are pre-determined or programmed at or very near the same level. Low Vac (306) and Low Threshold (304) are also pre-determined or programmed. The monitored vacuum line on the graph is 302. Starting at the left side of FIG. 3 and following monitored vacuum 302 to the right, as vacuum 302 rises during a procedure and reaches occlusion threshold 308 and Max Vac level 310, the system recognizes that an occlusion has occurred and a timer begins measuring the time. Additionally, the pump is typically turned off and the maximum allowable vacuum level is re-set to Low Vac, thereby reducing the monitored vacuum 302. In some embodiments, the Low Vac is not set until the threshold time has been reached. Alternately, the Low Vac may be set without waiting for a threshold time to pass, in which case a timer would not be needed. As the occlusion is cleared by whatever means, vacuum 302 begins to drop again until it falls below Low Threshold (304). At that point, the system recognizes that the occlusion has been cleared, and Max Vac (310) is re-set as the maximum allowable vacuum level. The monitored vacuum level 302 typically stays at the lower level in flow pump systems until another occlusion is encountered. When another occlusion is encountered, the vacuum 302 begins to rise again and the process stated above begins anew.

Note that graphical representations of embodiments including vacuum pumps wherein flow rate is sensed and used to control vacuum generally look like inverted versions of FIGS. 2 and 3 with the y-axis showing flow rate and without a Max Vac value.

The above embodiments and examples describe two vacuum levels (i.e. Max Vac and Low Vac), however other embodiments may include various intermediate levels and settings. For example, a middle vacuum level (Mid Vac) between Max Vac and Low Vac could be pre-determined or programmed. In such and embodiment, once monitored vacuum has risen above occlusion threshold for a set threshold period of time, the maximum allowable vacuum level is set to Mid Vac. If the occlusion is not cleared at Mid Vac after a second threshold period of time, then the maximum allowable vacuum level is set to Low Vac and held there until the occlusion is cleared. After occlusion clearance (i.e. once monitored vacuum has fallen below a Low Threshold, then the maximum allowable vacuum level may be re-set to either Mid Vac or Max Vac. By having one or more intermediate vacuum levels, a user has more control over the vacuum levels as well as the potential surge characteristics once an occlusion is cleared. In one embodiment, once an occlusion has been determined, the system may automatically begin lowering the maximum allowable vacuum level incrementally by pre-determined or programmed increments until the occlusion is cleared. In this latter embodiment, the vacuum could be maintained as close to Max Vac as possible throughout the procedure. As described above, these alternate embodiments are equally applicable to flow pump systems or combination pump systems.

One advantage of the embodiments described above is that surgeons can more safely and effectively utilize the full range of aspiration rates, vacuum pressures and flow rates available on typical surgical devices. For example, in typical phacoemuslification devices, the aspiration mechanisms may allow for vacuum or suction pressures during normal operation up to 650 mmHg or more. Typical current suction pressures may be in the range of 300 mmHg. Often, surgeons use the low end or middle of the available aspiration ranges in order to avoid unsafe fluidic surges during occlusion events. However, this means that they are typically treating at a slower rate because of the reduced aspiration flow. By utilizing the present invention, higher aspiration rates and vacuum levels may be used without fear of dangerous fluidic surges.

Methods in accordance with the present invention may be incorporated into or include software routines and modules and/or hardware and firmware in order to automatically carry out the method depicted with reference to FIG. 1. An input device, such as, for example, a mouse or keyboard, may be included in the system to facilitate user input of parameters and settings. Further, various storage media, such as, for example, CDs, DVDs, tape storage, magnetic, optical or electronic storage media, or other known storage media may be included to store settings.

Although there has been hereinabove described a specific application of vacuum as a method and mechanism for controlling eye chamber stability in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. The methods and embodiments of the present invention have generally been discussed with reference to opthalmology. However, the methods and embodiments have equal application to other medical arts, including those in which irrigation and aspiration are used in the excision, removal, movement, treatment, measurement and so on of tissue. Accordingly, any and all modifications, variations or equivalent arrangements which may occur to those skilled in the art, should be considered to be within the scope of the present invention as defined in the appended claims.

What is claimed is:

1. A phacoemulsification system, comprising:
    a handpiece configured to be placed in an operative relationship with an eye for a surgical procedure;
    an irrigation fluid source for supplying irrigation fluid to the eye;
    an aspiration source coupled to the handpiece in order to aspirate the irrigation fluid from the eye through the handpiece; and
    a control unit for controlling a vacuum in the handpiece, wherein the control unit is configured to control operation of the handpiece based on:
        an occlusion parameter, the occlusion parameter being a vacuum level or a flow rate; and
        a maximum allowable vacuum level in the handpiece, the maximum allowable vacuum level initially set to a first level;
    wherein the control unit is configured to reduce the maximum allowable vacuum level from the first level to a lower level a predetermined amount of time after detecting an occlusion based on the occlusion parameter, and the control unit is further configured to increase the maximum allowable vacuum level from the lower level to the first level when a current vacuum level is below the lower level.

2. The system of claim 1, further comprising a power source configured to provide power to the handpiece for performing the surgical procedure.

3. The system of claim 1, wherein the aspiration source is a flow pump or a combination of a vacuum pump and a flow pump.

4. The system of claim 1, wherein the occlusion parameter is a vacuum level corresponding to an occlusion of the handpiece or a flow rate corresponding to an occlusion of the handpiece.

5. A phacoemulsification system, comprising:
    a handpiece configured to be placed in an operative relationship with an eye for a surgical procedure;
    an irrigation fluid source for supplying irrigation fluid to the eye;
    an aspiration source coupled to the handpiece in order to aspirate the irrigation fluid from the eye through the handpiece; and
    a control unit for controlling a vacuum in the handpiece, wherein the control unit is configured to control operation of the handpiece based on:
        an occlusion parameter, the occlusion parameter being a vacuum level or a flow rate; and
        a maximum allowable vacuum level adjustable from a first level to a second level that is less than the first level;
    wherein the control unit is configured to reduce the maximum allowable vacuum level from the first level to the second level a determined amount of time after detecting an occlusion based on a current value of the occlusion parameter, and to increase the maximum allowable vacuum level from the second level to the first level when a current vacuum level is below the second level.

6. The system of claim 5, further comprising a power source configured to provide power to the handpiece for performing the surgical procedure.

7. The system of claim 5, wherein the aspiration source is a vacuum pump or a combination of a vacuum pump and a flow pump.

8. The system of claim 5, wherein the occlusion parameter is a vacuum level corresponding to an occlusion of the handpiece or a flow rate corresponding to an occlusion of the handpiece.

* * * * *